US00PP16486P2

(12) United States Plant Patent

Kowitz

(10) Patent No.: US PP16,486 P2

(45) Date of Patent: Apr. 25, 2006

(54) *CALAMAGROSTIS* PLANT NAMED 'ELDORADO'

(50) Latin Name: *Calamagrostis×acutiflora*
Varietal Denomination: Eldorado

(76) Inventor: Todd Erin Kowitz, 38 Mink Creek Rd., Kettle Falls, WA (US) 99141

( * ) Notice: Subject to any disclaimer, the term of this patent is extended or adjusted under 35 U.S.C. 154(b) by 89 days.

(21) Appl. No.: 11/018,135

(22) Filed: Dec. 20, 2004

(51) Int. Cl.
*A01H 5/00* (2006.01)

(52) U.S. Cl. ..... Plt./384

(58) Field of Classification Search ..... Plt./384
See application file for complete search history.

*Primary Examiner*—Anne Marie Grunberg
(74) *Attorney, Agent, or Firm*—Penny J. Aguirre

(57) ABSTRACT

A new cultivar of Feather reed grass, *Calamagrostis×acutiflora* 'Eldorado', characterized by its variegated foliage with golden yellow centers and green margins, golden colored rachis, cold hardiness to USDA Zone 4 and its vigorous growth habit with tolerance to a range of growing conditions.

2 Drawing Sheets

Botanical classification: *Calamagrostis×acutiflora.*
Varietal denomination: 'Eldorado'.

BACKGROUND OF THE INVENTION

The present invention relates to a new and distinct cultivar of *Calamagrostis×acutiflora* and will be referred to hereafter by its cultivar name, 'Eldorado'. 'Eldorado' represents a new cultivar of Feather reed grass, a cold hardy, perennial ornamental grass grown for landscape use.

The inventor discovered and selected the new cultivar, 'Eldorado', in a greenhouse at his nursery in Kettle Falls, Wash. in November of 2000. 'Eldorado' was discovered growing in a 4" container than had been planted in the spring of 2000 with divisions of *Calamagrostis×acutiflora* 'Karl Foerster' (not patented). 'Eldorado' is therefore presumed to be a culm sport of 'Karl Foerster'.

The new cultivar 'Eldorado' was selected for the unique variegation pattern to its leaf blades of golden yellow centers and green margins. The foliage of 'Karl Foerster' is not variegated. 'Eldorado' can also be distinguished from 'Karl Foerster' in having rachis that are more golden in color and inflorescences that are more elongated and irregular in height. In comparison to two other cultivars of *Calamagrostis* that are known to the inventor to have variegated foliage, 'Overdam' (not patented) and 'Avalanche' (not patented), 'Eldorado' has golden yellow variegation, whereas 'Overdam' has foliage with creamy white variegation with less uniformity and 'Avalanche' has foliage that is variegated with white.

Asexual reproduction of the new cultivar was first accomplished by culm division in Kettle Falls, Wash. in spring of 2001 by the inventor. The characteristics of this cultivar have been determined to be stable and are reproduced true to type in successive generations.

SUMMARY OF THE INVENTION

The following traits have been repeatedly observed and represent the characteristics of the new cultivar. The new Feather reed grass has not been observed under all possible environmental conditions. The phenotype may vary somewhat with variations in temperature, day-length, light intensity, soil types, and water and fertility levels without, however, any variance in genotype. The general observations, and descriptions that follow describe plants that were grown outdoors in Kettle Falls, Wash. for a period of three years. These attributes in combination distinguish 'Eldorado' from all other selections of Feather reed grass known to the inventors.

1. The foliage of 'Eldorado' exhibits a unique variegation pattern that exhibits golden yellow centers with green margins.
2. The rachis of the inflorescences are golden in color.
3. 'Eldorado' starts blooming in late May with inflorescences that persist into winter.
4. 'Eldorado' is hardy to USDA Zone 4 and grows well in any reasonably moist soils, including heavy clay, in full sun to partial shade.

BRIEF DESCRIPTION OF THE DRAWING

The accompanying colored photographs illustrate the overall appearance and distinct characteristics of the new Feather reed grass. The photographs were taken in September and represent plants grown outdoors in Zeeland, Mich. from an 8-inch division for one growing season.

Figure 1:
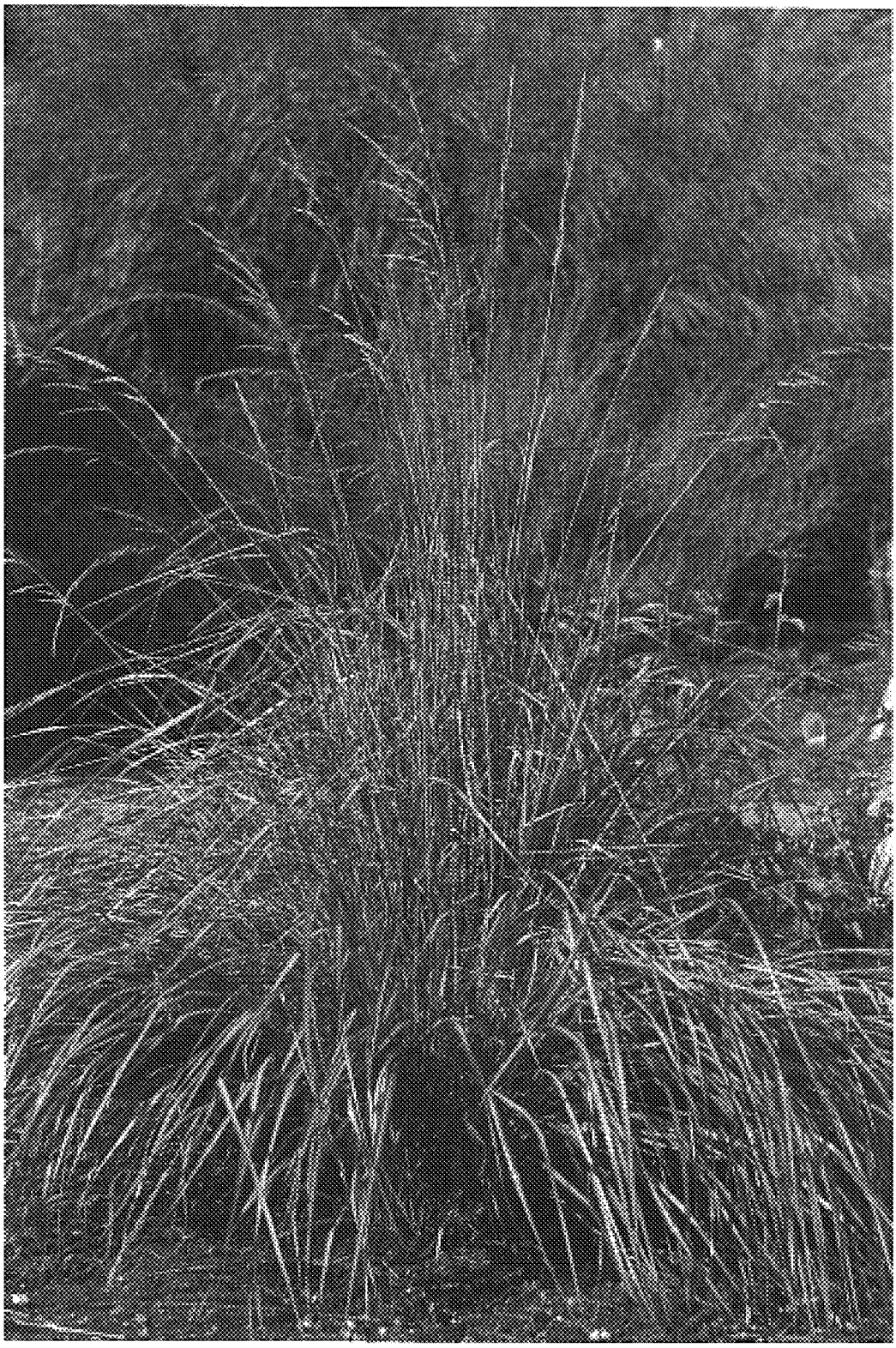
FIG. 1 illustrates the overall habit and appearance of 'Eldorado'.
Figure 2:
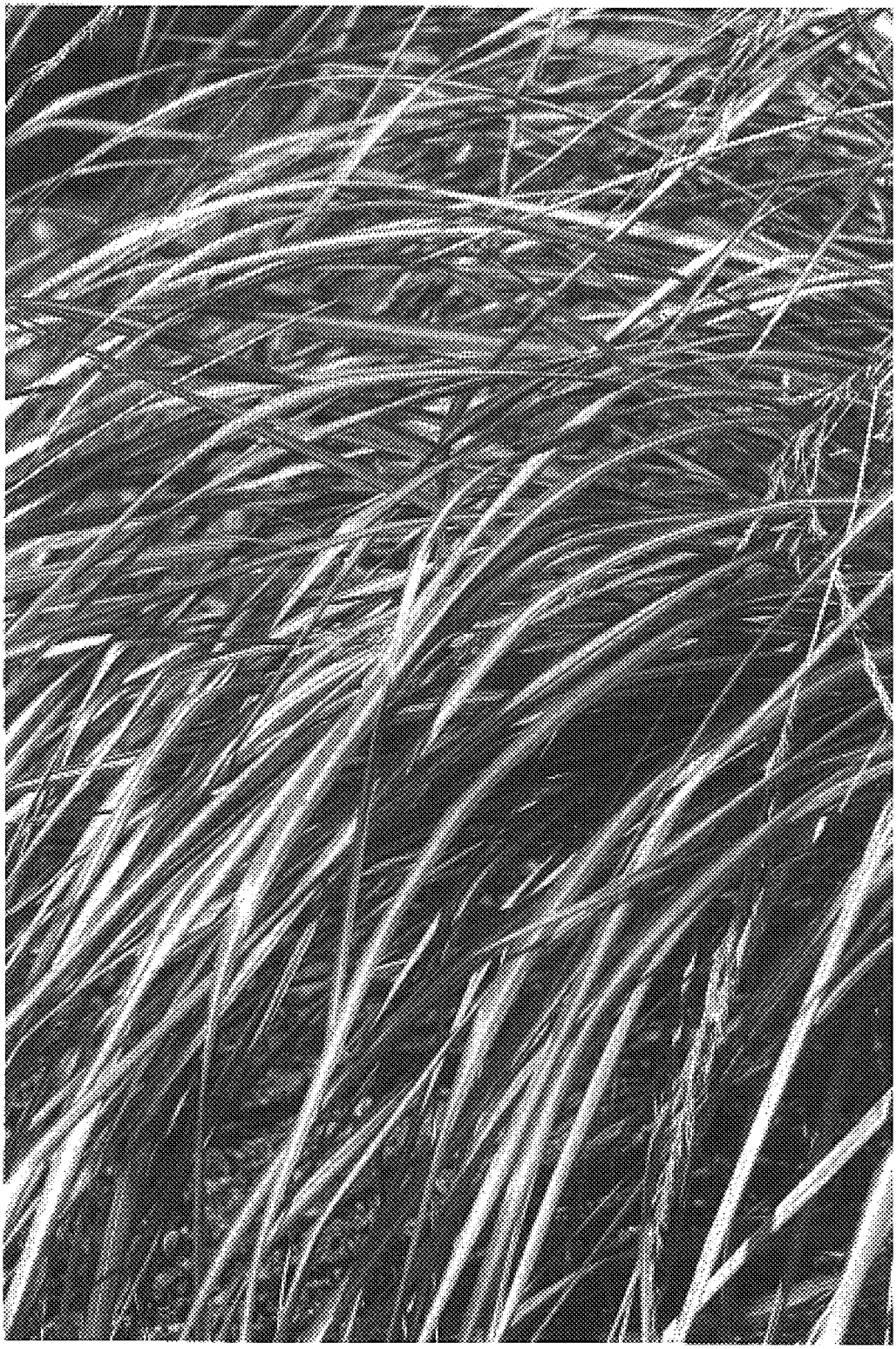

The photograph of FIG. 2 is a close-up view of the variegated foliage characteristic of 'Eldorado'.

The colors in the photographs are as close as possible with the photographic and printing technology utilized. The color values cited in the detailed botanical description accurately describe the colors of the new *Calamagrostis.*

DETAILED BOTANICAL DESCRIPTION

The general observations are based on plants grown in an outdoor trial bed for 3 years in Kettle Falls, Wash., while the detailed botanical data describe plants that were grown outdoors in Zeeland, Mich. from an 8-inch division for one growing season. The color determinations are in accordance with the 2001 RHS Colour Chart of The Royal Horticultural Society, London, England, except where general color terms of ordinary dictionary significance are used.

Botanical classification: 'Eldorado' is a cultivar of *Calamagrostis×acutiflora*. *Calamagrostis×acutiflora* is a hybrid between *Calamagrostis epigegos* and *Calamagrostis arundinacea*.

Common name: 'Eldorado' Feather reed grass.

Parentage: Naturally occurring culm sport of *Calamagrostis×acutiflora* 'Karl Foerster'.

General description:

*Blooming period.*—Bloom begins in early to mid summer in the Northeast U.S., flowers are retained over the winter.

*Plant habit.*—Herbaceous, clump-forming, ornamental grass with an upright flowering culms surrounded by non-flowering culms with cascading foliage.

*Height and spread.*—Reaches a height of about 1.5 m to 1.8 m (5 to 6 ft) and a spread at the base of about 30 cm (12 in) with leaves cascading to about 60 to 90 cm (2 to 3 ft) in diameter.

*Cold hardiness.*—To at least USDA Zone 4.

*Culture.*—Grows best in full sun to part shade in fertile, well-drained soils with adequate moisture, tolerates heavy clay.

*Diseases and pests.*—No unique aspects concerning susceptibility or resistance to diseases or pests that affect *Calamagrostis* have been observed.

*Root description.*—Fibrous.

Growth and propagation:

*Propagation.*—Culm division, best divided in spring when in active growth.

*Time required for root development.*—A 32-cell liner will fully develop in a one-gallon container in 6 to 8 weeks when grown in a greenhouse under ambient light and temperature in Kettle Falls, Wash.

*Growth rate.*—Vigorous.

Culm (stem) description:

*General.*—Cylindrical but slightly flattened (ovoid), completely enclosed by leaf sheaths with bare culms exposed between point where leaf blades attaches and next node and between last leaf blade and inflorescence. Numerous basal culms with cascading leaves emerge throughout the season with flowering culms emerging from the center of the plant.

*Culm aspect.*—Rigid and held erect or cascading up to a 45° from apex.

*Culm color.*—144A (bare), 138A (sheathed).

*Culm size.*—Flowering culms; up to about 4 mm in diameter at base, tapering to about 2 mm in diameter at base of inflorescence, up to about 1.2 m (4 feet) in height to tip of inflorescence. Non-flowering culms are up to 3 mm in diameter, up to 20 cm in length (up to 50 cm to tip of terminal leaf).

*Culm surface.*—Glabrous with fine vertical ridges.

*Internode length.*—About 14 to 30 cm between nodes, leaf sheaths are about 25 cm in length from node to leaf blade attachment, an area about 3 mm width and N144A in color encircles the entire culm at node.

Foliage description:

*Leaf shape.*—Linear.

*Leaf division.*—Simple.

*Leaf base.*—Sheathed to node.

*Leaf apex.*—Acute, tapering to a fine point.

*Leaf aspect.*—Leaf blades diverge from leaf sheath at ligule at up to a 20° to 30° angle from center of culm and the upper one-third of the leaf blade cascades downward.

*Leaf venation.*—Parallel, not conspicuous, color matches the color of the leaf blades on both surfaces.

*Leaf margins.*—Entire, with sharp short bristles that are not visually noticeable.

*Leaf persistence.*—Foliage dries but is persistent throughout the winter.

*Leaf attachment.*—Sheathed to culm node.

*Ligule.*—Leaf-like, on upper surface of leaf blade only, about 1.5 mm in length on basal foliage and 155A in color on basal foliage, papery and up to 5 mm in length on culm foliage, 164D in color.

*Leaf size.*—Non-flowering culm foliage; sheathed portion is about 15 cm in length, leaf blades up to about 30 cm in length and up to about 1 cm in width tapering to a point at the apex. Flowering culm foliage; sheathed portion is about 15 to 30 cm in length, leaf blades are about 18 to 25 cm in length and up to about 1.5 cm in width.

*Leaf surface.*—Glabrous on upper and lower surface, upper surface of newly formed basal foliage has a satiny sheen, sharp bristles on margins (not visible).

*Leaf number.*—About 2 to 3 per flowering culm, 3 to 4 on basal stems.

*Leaf arrangement.*—Alternate.

*Leaf color and variegation description.*—Variegation pattern is composed of green margins ranging from 1 mm to 3 mm in width and golden yellow centers ranging from 1 to 4 mm in width, narrow green stripes may be present in center and narrow yellow stripes may be present in margins. New growth, upper and lower surfaces; centers N144A to N144B, margins 138A. Mature growth, upper and lower surface; centers lighten to 162D, margins darken to 137A. All foliage dries to a color between 165B and 165C in late fall and is retained through winter, the foliage of the flowering culms dries earlier, in September, when the flower color changes to beige.

Flower description:

*General description.*—Compact panicle terminating from flowering culms in summer, composed of numerous slender upright racemes, spikelets typically arranged in two equal pairs, 1 flowers per spikelet.

*Longevity of inflorescence.*—Panicles are persistent from fall through winter.

*Fragrance.*—None.

*Panicle size.*—Typically 15 to 30 cm in length and 3 cm in width, racemes range from 4 to 7 cm in length and are about 0.5 cm in width.

*Panicle color.*—Emerges with a coppery red cast over green (effectively tinged 178A, greyed red) and changes to a beige color by late summer, closest to 199D.

*Rachis color.*—165C.

*Spikelet size.*—About 4 mm in length and 1 mm in width.

*Spikelet description.*—1 floret per spikelet, 2 glumes 4 mm in length, 1 mm in width, palea is shorter and translucent, lemma is 3 mm in width, 0.75 mm in width with awn extending to 1 cm, numerous very fine hairs extend from base of lemma to 2 mm, glumes and lemma were papery and closest to 199D in color.

Reproductive organs:

*Androecium.*—Anthers and therefore pollen were not visible on the plants observed.

*Gynoecium.*—Pistil; 1, 2 plumose stigmas, stigma color is N187A. Ovary; 1-locular, superior, minute, not easily quantifiable in size and color.

*Caryopsis.*—Presumed sterile (*Calamagrostis*× *acutiflora* hybrids are typically sterile), seed set has not been observed.

I claim:

1. A new and distinct cultivar of *Calamagrostis* plant named 'Eldorado' as herein illustrated and described.

* * * * *